(12) United States Patent
Huang et al.

(10) Patent No.: US 11,642,116 B2
(45) Date of Patent: May 9, 2023

(54) SURGICAL RETRACTOR

(71) Applicant: Eped, Inc., Kaohsiung (TW)

(72) Inventors: Ta-Ko Huang, Kaohsiung (TW); Jerry T. Huang, Industry, CA (US)

(73) Assignee: EPED, INC., Kaohsiung (TW)

( * ) Notice: Subject to any disclaimer, the term of this patent is extended or adjusted under 35 U.S.C. 154(b) by 0 days.

(21) Appl. No.: 17/845,292

(22) Filed: Jun. 21, 2022

(65) Prior Publication Data
US 2023/0038650 A1  Feb. 9, 2023

(51) Int. Cl.
*A61B 17/02* (2006.01)
*A61B 1/32* (2006.01)
*A61B 90/50* (2016.01)

(52) U.S. Cl.
CPC ............. *A61B 17/02* (2013.01); *A61B 1/32* (2013.01); *A61B 90/50* (2016.02)

(58) Field of Classification Search
CPC . A61B 17/02; A61B 17/0206; A61B 17/0281; A61B 17/0293; A61B 1/32; A61B 90/50; A61B 2017/0287
See application file for complete search history.

(56) References Cited

U.S. PATENT DOCUMENTS

| | | | | |
|---|---|---|---|---|
| 5,222,951 A | * | 6/1993 | Abidin | A61B 17/30 30/162 |
| 5,931,850 A | * | 8/1999 | Zadini | A61B 17/0218 604/98.01 |
| 9,138,218 B2 | * | 9/2015 | Picha | A61B 17/0293 |
| 9,402,610 B2 | * | 8/2016 | Pell | A61B 17/0206 |

FOREIGN PATENT DOCUMENTS

| | | |
|---|---|---|
| CN | 113040891 A | 6/2021 |
| WO | 2018098345 A1 | 5/2018 |

* cited by examiner

Primary Examiner — Zade Coley
Assistant Examiner — Tracy L Kamikawa
(74) Attorney, Agent, or Firm — Schmeiser, Olsen & Watts LLP

(57) ABSTRACT

A surgical retractor includes a mounting base, a first rod member, a connecting member, a compression spring, a second rod member, an expansion member, an extension spring and a position member. One end of the first rod member is assembled on the mounting base, and the other end of the first rod member includes a blocking part; the connecting member is assembled on the first rod member and includes a shoulder and a first connecting part; the compression spring is arranged on the connecting member and abuts against the shoulder and the blocking part; the second rod member is slidably arranged on the first rod member; the expansion member is arranged at the end of the second rod member and includes a second connecting part; an extension spring connects the first connecting part and the second connecting part; a position member selectively abuts against the first rod member.

6 Claims, 14 Drawing Sheets

SURGICAL RETRACTOR

BACKGROUND OF THE INVENTION

Related Application

This application claims priority to Taiwanese patent application number 110127063, filed on Jul. 22, 2021, the entirety of which is incorporated by reference herein.

Field of the Invention

The present invention relates to a surgical retractor, in particular to a surgical retractor that automatically can adjust the expansion position to achieve the purpose of improving the convenience of use.

Description of Related Art

The surgical retractor is an auxiliary tool for medical surgery. During the operation, the surgical retractor can be used to expand the human tissue at the surgical site to facilitate the operation of medical personnel.

Currently known surgical retractors mainly include a rod body and an expansion device (such as expansion blades, expansion calipers, etc.). The rod body can be installed on external equipment such as operating tables, the expansion device is slidable on the rod body and it is slidingly relative to the rod body. When the expansion device is used to expansion the human tissue of the surgical site in a position, the expansion device is locked on the rod body.

As mentioned above, the traditional expansion device must use human power to adjust and lock the position, but the opening size of the human tissue at the surgical site will constantly change during the operation. At this time, the expansion device must also be constantly adjusted by human power to match the ever-changing opening size, that is, the expansion device must be repeatedly loosened and slidable to a position before being locked.

Therefore, it can be known that the above-mentioned traditional surgical retractor will cause a burden on medical personnel during the operation, and it is extremely inconvenient to use.

SUMMARY OF THE INVENTION

In order to solve the problems of the above-mentioned traditional surgical retractor, the present invention provides a surgical retractor, which includes a mounting base, a first rod member, a connecting member, a compression spring, and a second rod member, an expansion member, an extension spring and a position member.

One end of the first rod member is assembled on the mounting base, and the other end of the first rod member includes a blocking part; the connecting member is assembled on the first rod member, and the connecting member includes a shoulder and a first connecting part; the compression spring is arranged on the connecting member and abuts against the shoulder and the blocking part; the second rod member is slidably arranged on the first rod member and slides relative to the first rod member, and one end of the second rod member slides and extends relative to the first rod member; the expansion member is assembled at the end, and the expansion member includes a second connecting parts; the extension spring connects the first connecting part and the second connecting part; the position member is assembled on the second rod member and selectively abuts against the first rod member.

With the above-mentioned structural design, the surgical retractor provided in the present invention can automatically adjust the expansion position to achieve the purpose of improving the convenience of use.

In one embodiment, the mounting base includes a fixing base and a clamping arm, and the clamping arm extends outward from the fixing base. The aforementioned clamping arm can be clamped and fixed to an external device such as an operating table.

In one embodiment, the first rod member includes the end of the blocking part where a blocking piece is fixedly thereof, and the blocking part is formed on the blocking piece. The aforementioned blocking piece can be fixed by welding, snapping, etc., for example.

In one embodiment, the first rod member includes a sliding groove, the second rod member includes a sliding key, and the second rod member is slid on the first rod member by the sliding key corresponding to the sliding groove. The aforementioned sliding groove and the sliding key can also be arranged oppositely, that is, the first rod member may include a sliding key, and the second rod member may include a sliding groove.

In one embodiment, the sliding key includes a blocking protrusion, and the blocking protrusion is blocked by the blocking piece. In other words, when the first rod member and the second rod member are relatively sliding, the blocking protrusion can be used to stop the blocking piece to prevent the problem of the first rod member and the second rod member from being separated each other due to accidental application of excessive force.

In one embodiment, the sliding key includes a gear control member, and the gear control member is selectively arranged at different positions of the sliding key and selectively blocked by the block piece. With the arrangement of the gear position control member, the second rod member can have a gear position control effect with different sliding distances when the second rod member slides relative to the first rod member.

In one embodiment, the gear control member is a screw, of course, it can also be a structural design such as a bolt or a locking pin.

In one embodiment, the connecting member includes a series part and a parallel part, the series part is formed with the shoulder and the first connecting part; the compression spring includes a left compression spring and a right compression, and the left compression spring and the right compression spring are arranged at the parallel part in parallel.

In one embodiment, the expansion member includes an expansion blade, a suction tube, and a fixing member that are assembled with each other, and the fixing member is formed with the second connecting part. The aforementioned suction tube can be connected with a suction line to discharge the exhaust gas generated during the operation (for example, using electric burning).

In one embodiment, the position member is a knob, and the knob is screwed on the second rod member and selectively abuts against the first rod member. The aforementioned knob can also be a structural design such as a clamping arm and a locking pin.

In one embodiment, the first rod member and the second rod member are each a tubular member, and the second rod is a tube-sleeved outside the first rod member.

The present invention provides another surgical retractor, which includes a mounting base, a sliding sheet, an expansion member, a shaft member, two connecting rod members, and a bush. Wherein, the mounting base defines a longitudinal direction and includes a blade body; the sliding sheet is attached to the mounting base and slides along the longitudinal direction relative to the mounting base; the expansion member includes two expansion blades, the two expansion blades are respectively disposed on opposite sides of the mounting base and pivoted relative to the mounting base; the shaft is attached to the mounting base and slides along the longitudinal direction relative to the mounting base and rotates around the longitudinal direction, and the shaft member includes a shaft cam, the shaft cam electively abuts against the blade body; the two connecting rod members are respectively connected between the shaft member and the two expansion blades; the bush is arranged on the mounting base and rotates around the longitudinal direction, and the bush includes a bush cam, the bush cam selectively abuts against the blade body.

In one embodiment, the mounting base is provided with a hollow rod member along the longitudinal direction; the surgical retractor further includes a suction tube, a part of the suction tube is attached in the hollow rod member and slides relative to the hollow rod member.

In one embodiment, the sliding sheet is provided with a suction tube clamp, and the suction tube clamp clamps the suction tube.

In one embodiment, the shaft member and the bush are arranged coaxially.

DETAILED DESCRIPTION

Figure 1:
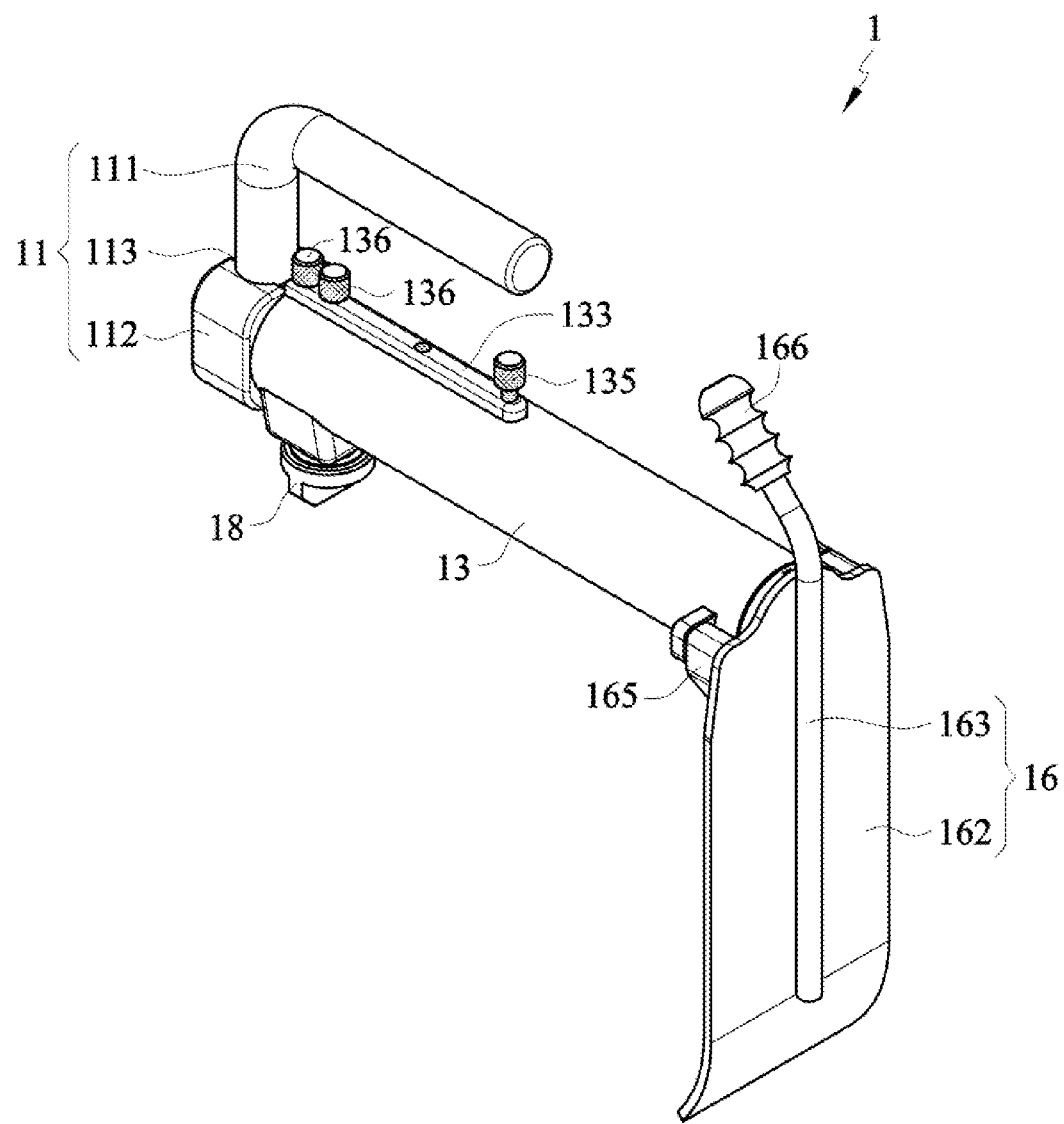
FIG. 1 is a perspective view of a preferred embodiment of the present invention.
Figure 2:
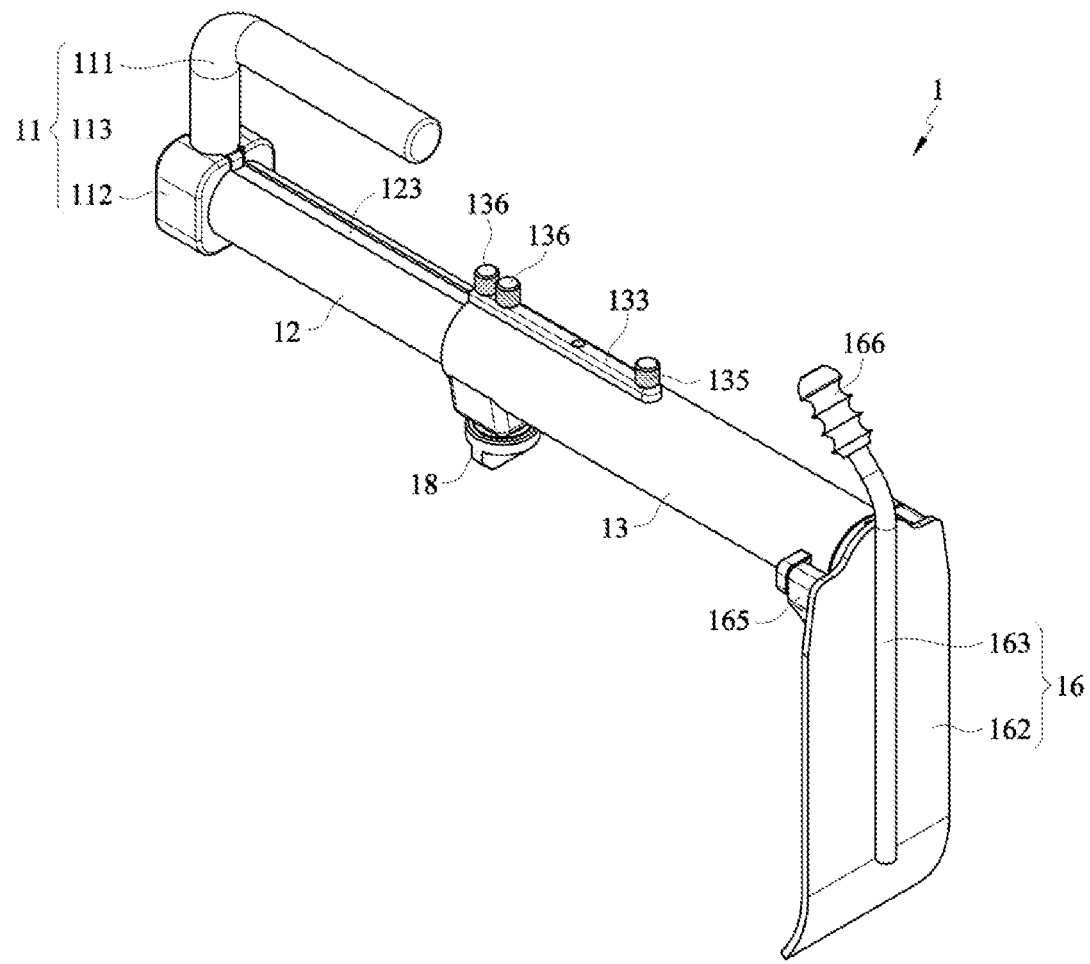
FIG. 2 is another perspective view of the preferred embodiment of the present invention.
Figure 3:
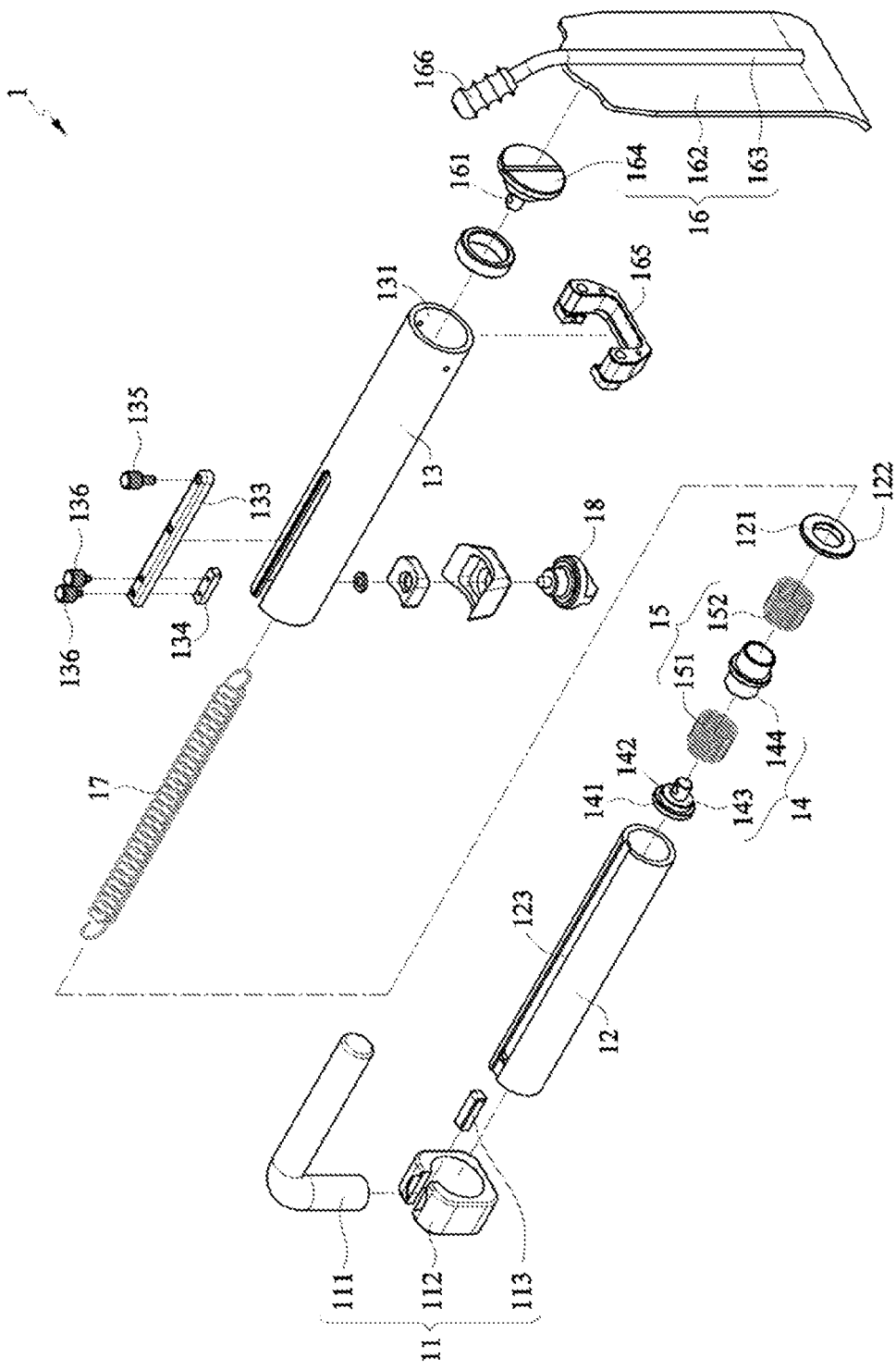
FIG. 3 is an exploded view of a preferred embodiment of the present invention.
Figure 4:
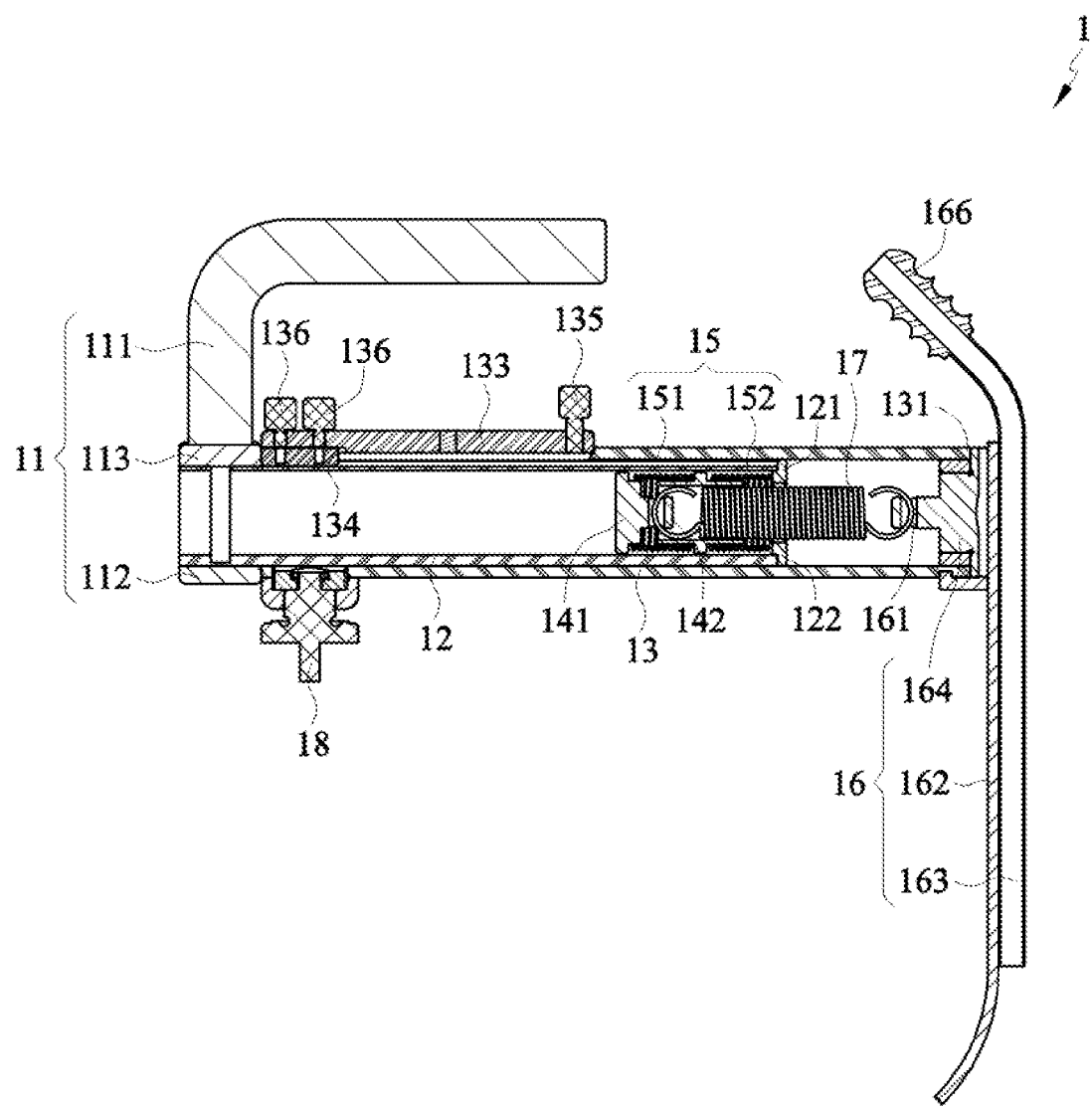
FIG. 4 is a cross-sectional view of a preferred embodiment of the present invention.
Figure 5:
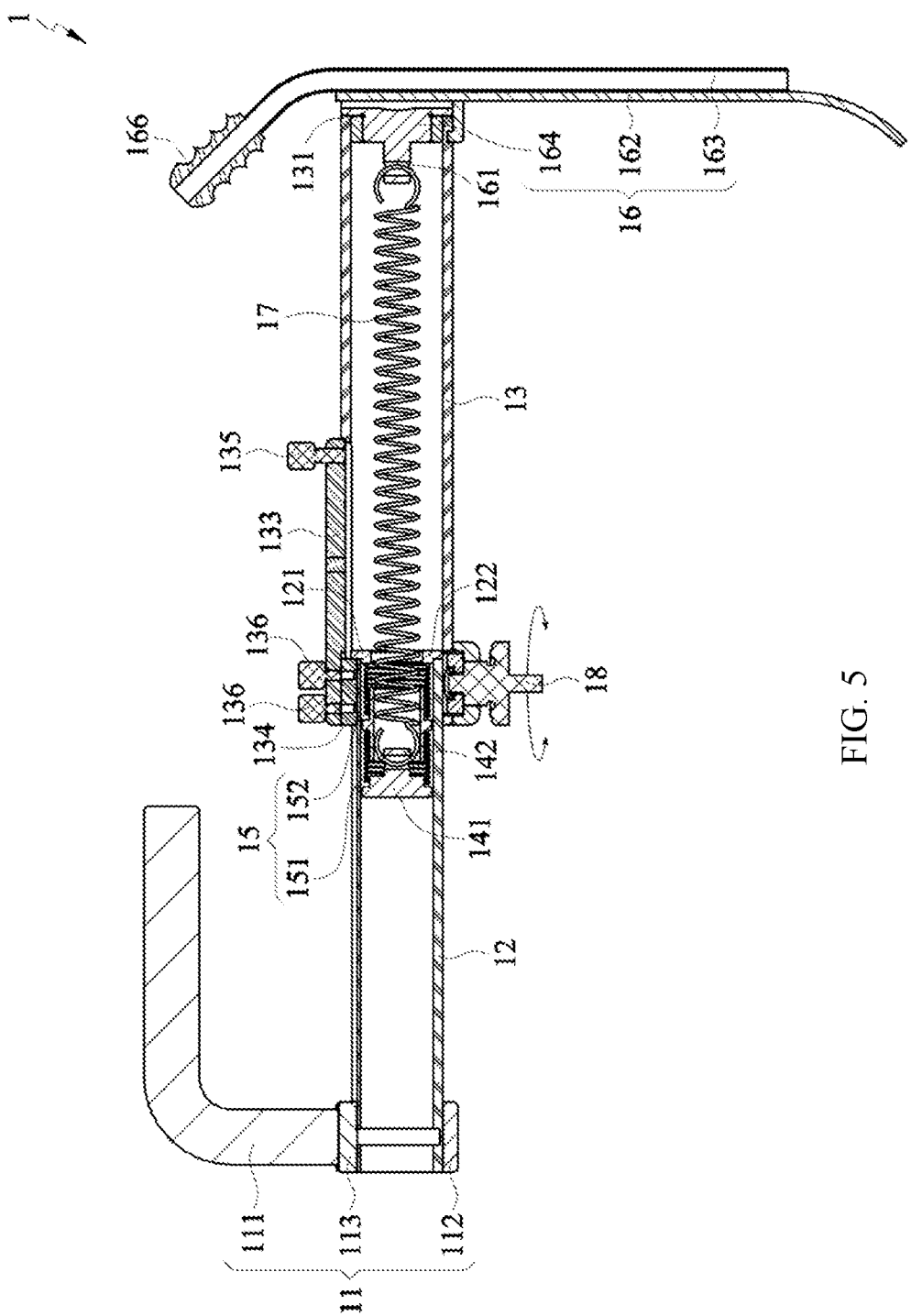
FIG. 5 is another cross-sectional view of the preferred embodiment of the present invention.

Please refer to FIGS. 1 to 5 at the same time, wherein FIG. 1 is a perspective view of a preferred embodiment of the present invention, FIG. 2 is another perspective view of a preferred embodiment of the present invention, and FIG. 3 is an exploded view of a preferred embodiment of the present invention. The exploded view of the preferred embodiment, FIG. 4 is a cross-sectional view of the preferred embodiment of the present invention, and FIG. 5 is another cross-sectional view of the preferred embodiment of the present invention.

A surgical retractor 1 is shown in FIGS. 1 to 5, and the surgical retractor 1 includes a mounting base 11, a first rod member 12, a connecting member 14, a compression spring 15, a second rod member 13, an expansion member 16, an extension spring 17 and a position member 18.

In this embodiment, the first rod member 12 and the second rod member 13 are respectively a tubular member, such as a circular tubular member as shown in the drawings, and the second rod member 13 is sleeved on the outside of the first rod member 12, at the same time, the second rod member 13 is slidably disposed on the first rod member 12 and slides relative to the first rod member 12, and when the second rod member 13 slides relative to the first rod member 12, one end 131 of the second rod member 13 slides and extends out relative to the first rod member 12. In the accompanying drawings, FIGS. 1 and 2 are perspective views showing the second rod member 13 sliding to different positions relative to the first rod member 12 (return to zero position in FIG. 1 and the open position in FIG. 2). FIGS. 4 and 5 are cross-sectional views showing different sliding positions corresponding to FIGS. 1 and 2.

In terms of structural design, the first rod member 12 and the second rod member 13 are not limited to the circular tubular member described in this embodiment, that is, the first rod member 12 and the second rod member 13 can be any rod-shaped body, and its cross-section is not limited to any shape.

In addition, as shown in FIGS. 1 to 5, one end of the first rod member 12 is assembled on the mounting base 11, and the other end of the first rod member 12 includes a blocking part 121 where a blocking piece 122 is fixedly thereof, and the blocking part 121 is formed on the blocking piece 122. The aforementioned blocking piece 122 can be fixed by welding, snapping, etc., for example.

In this embodiment, the mounting base 11 includes a fixing base 112 and a clamping arm 111, and the clamping arm 111 extends outward from the fixing base 112. The aforementioned fixing base 112 is provided with a limiting block 113, which can be used to limit the sliding position of the second rod member 13 relative to the first rod member 12. In addition, the aforementioned clamping arm 111 can be used to be clamped and fixed to an external device such as an operating table (not shown).

In the structural design of the relative sliding movement of the first rod member 12 and the second rod member 13, as shown in the figure, the first rod member 12 includes a sliding groove 123, and the second rod member 13 includes a sliding key 133. The second rod member 13 is slidably disposed on the first rod 12 by sliding the sliding key 133 to the sliding groove 123 correspondingly. The aforementioned sliding key 133 includes a blocking protrusion 134. The blocking protrusion 134 is screw-locked to the sliding key 133 with two screws 136, and the blocking protrusion 134 is blocked by the blocking piece 122. That is, when the first rod member 12 and the second rod member 13 slide relatively, the blocking protrusion 134 can block the blocking piece 122 to prevent the first rod member 12 and the second rod member 13 from being disengaged by excessive force. The sliding distance of the second rod member 13 relative to the first rod member 12 can be limited.

As shown in FIGS. 1 to 5, the connecting member 14 is assembled to the first rod member 12, and the connecting member 14 includes a shoulder 141 and a first connecting part 142, and the compression spring 15 is arranged on the connecting member 14 and abuts against the shoulder 141 and the blocking part 121 of the first rod member 12.

In this embodiment, the connecting member 14 includes a series part 143 and a parallel part 144, and the series part 143 is formed between the aforementioned shoulder 141 and the first connecting part 142; the compression spring 15 includes a left compression spring 151 and a right compression spring 152, and the left compression spring 151 and the right compression spring 152 are arranged in parallel at the parallel part 144 of the connecting member 14.

In addition, the expansion member 16 shown in FIGS. 1 to 5 is assembled at the end 131 of the second rod member 13, for example, an assembly seat 165 is assembled at the end 131 of the second rod member 13, and the expansion member 16 includes a second connecting part 161; the extension spring 17 connects the first connecting part 142 and the second connecting part 161; the position member 18 is assembled to the second rod member 13 and selectively abuts against the first rod member 12.

In this embodiment, the expansion member 16 includes an expansion blade 162, a suction tube 163, and a fixing member 164, and the fixing member 164 is formed with a second connecting part 161. In addition, the position member 18 is a knob, and the knob is screwed on the second rod member 13 and selectively screwed against the first rod member 12.

Figure 6:
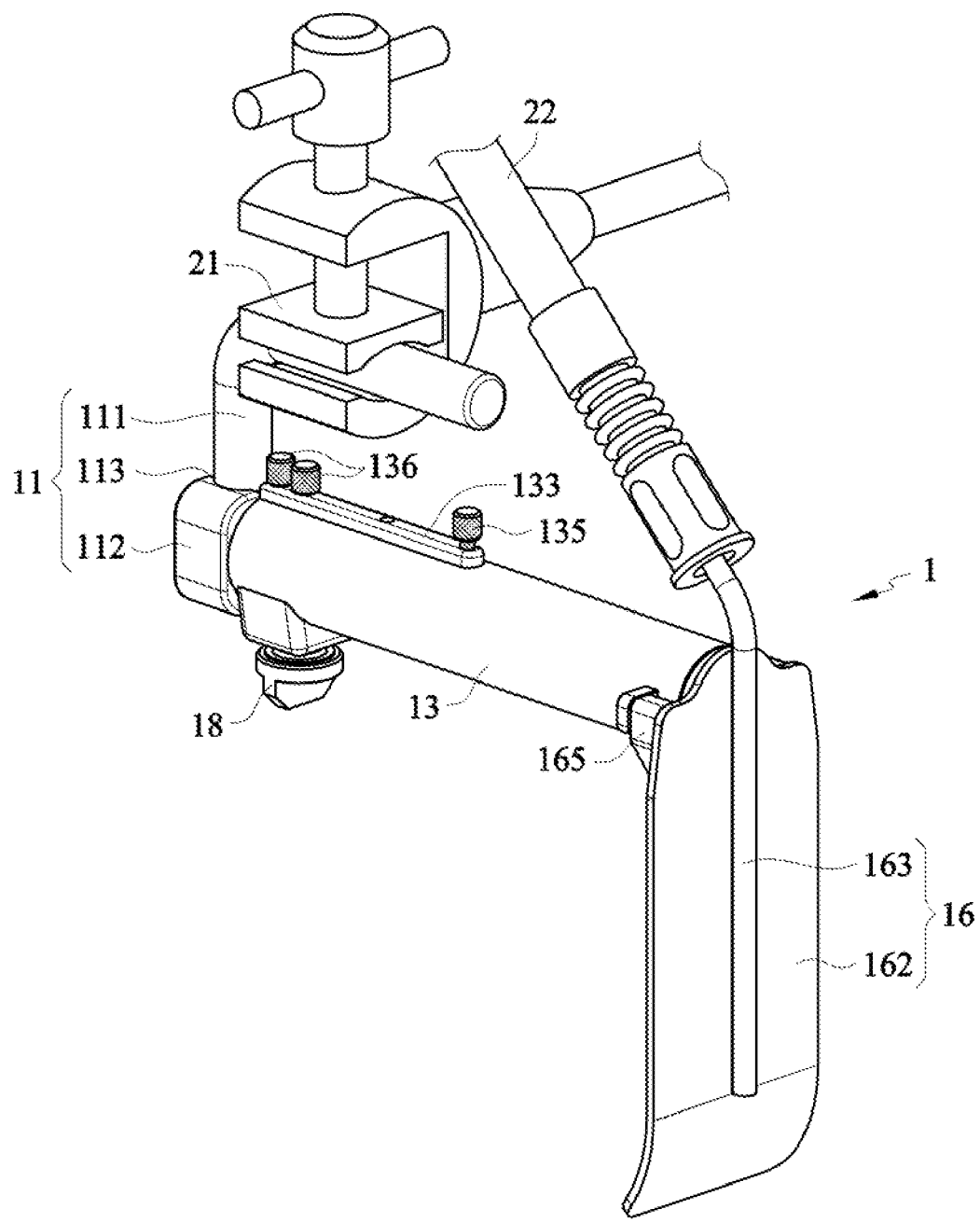
FIG. 6 is one of the schematic diagrams of the use state of the preferred embodiment of the present invention.
Figure 7:
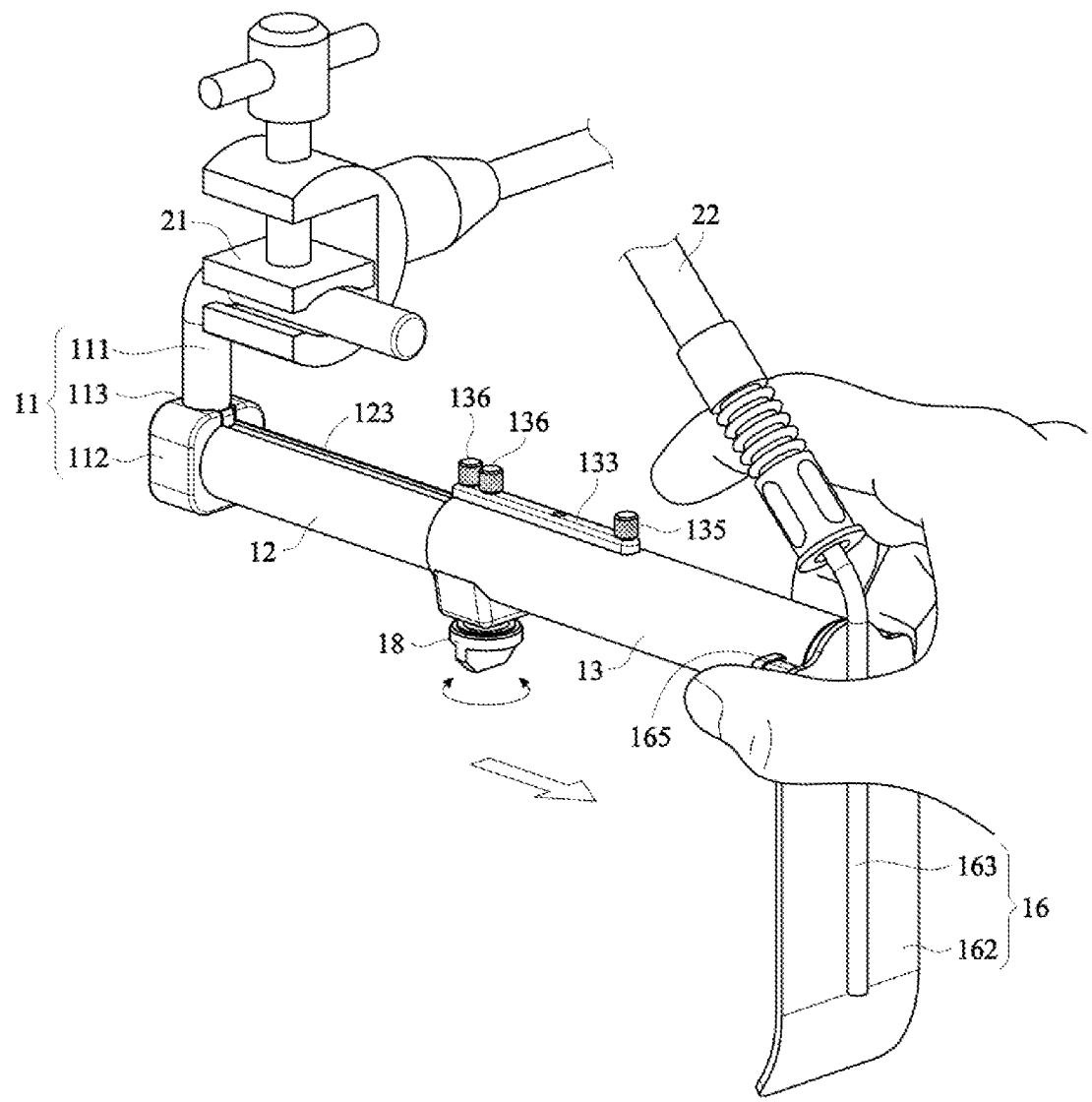
FIG. 7 is the second schematic diagram of the use state of the preferred embodiment of the present invention.

Please refer to FIGS. 6 and 7 at the same time. FIG. 6 is one of the schematic diagrams of the use state of the preferred embodiment of the present invention, and FIG. 7 is the second schematic diagram of the use state of the preferred embodiment of the present invention. Please also refer to FIG. 1 to FIG. 5.

In use, the clamping arm 111 can be clamped and fixed to the holder 21 of an external device such as an operating table (not shown), and the suction tube 163 is connected to a suction line 22. The connecting part 166 of the suction tube 163 for connecting the suction line 22 has a wavy shape, so that the suction tube 163 can be tightly connected to the suction line 22 to prevent fluid leakage. Then, as shown by the directional arrow in FIG. 7, the second rod member 13 is forced to slide to a position relative to the first rod member 12, that is, the second rod member 13 slides to the human tissue at the surgical site (not shown in the figure), and make the expansion blade 162 abut the human tissue of the surgical site. The expansion blade 162 is expanded and the elastic force of the compression spring 15 is used. Then, the extension spring 17 expands the human tissue of the surgical site to facilitate the operation of medical staff.

During the operation, the size of the opening of the human tissue at the surgical site may be constantly changing. The elastic force of the compression spring 15 and the extension spring 17 can be used to continuously abuts the human tissue at the surgical site where the expansion blade 162 keeps it open. In other words, the medical staff does not need to constantly adjust the surgical retractor 1 by human power during the operation, that is, the medical staff can concentrate on the operation.

Therefore, it can be seen from the above that, with the above structural design, the surgical retractor 1 can automatically adjust the expanding position to achieve the purpose of improving the convenience of use.

In addition, if it is desired to fix the expansion blade 162 at a certain position, after the second rod member 13 slides to the aforementioned position relative to the first rod member 12, the position member 18 (in this embodiment, is the knob) abuts (in this embodiment, the screw is turned and pressed, as shown by the rotating arrow in FIGS. 5 and 7) the first rod member 12, so that the second rod member 13 can be fixed relative to the first rod member 12 at the aforementioned position, that is, the expansion blade 162 can be fixed at the aforementioned position.

Figure 8A:
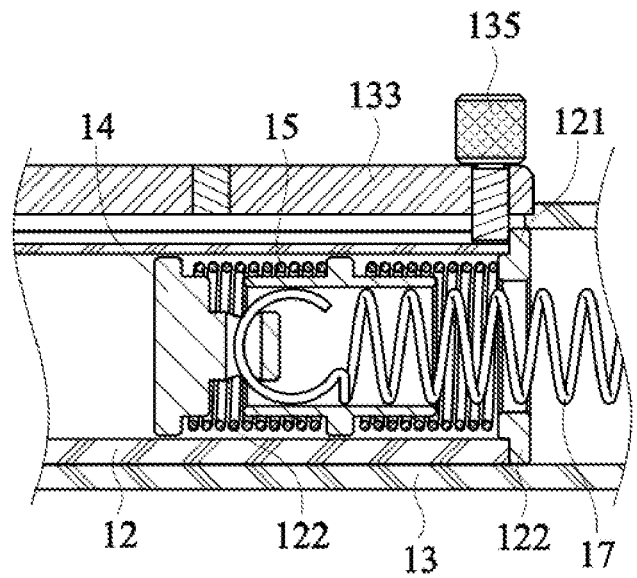
FIG. 8A is one of the schematic diagrams of the first gear change of the preferred embodiment of the present invention.
Figure 8B:
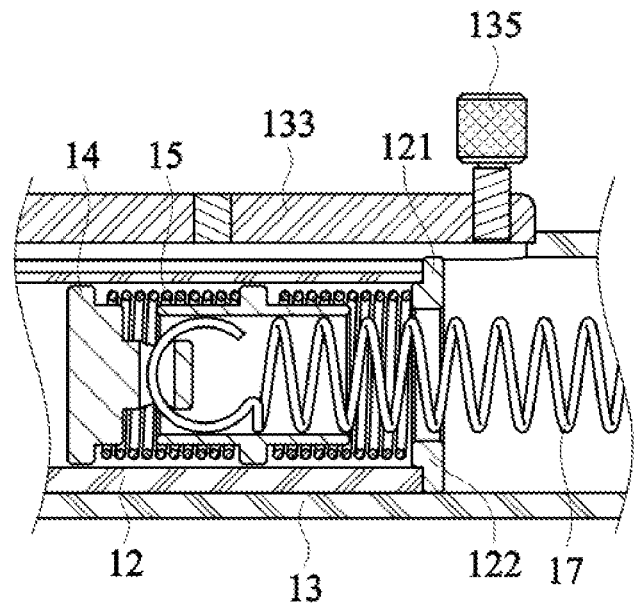
FIG. 8B is the second schematic diagram of the first gear change of the preferred embodiment of the present invention.
Figure 9A:
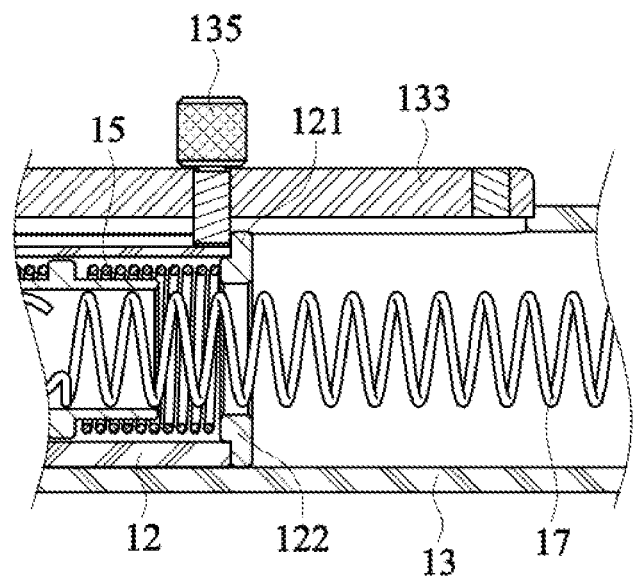
FIG. 9A is one of the schematic diagrams of the second gear change of the preferred embodiment of the present invention.
Figure 9B:
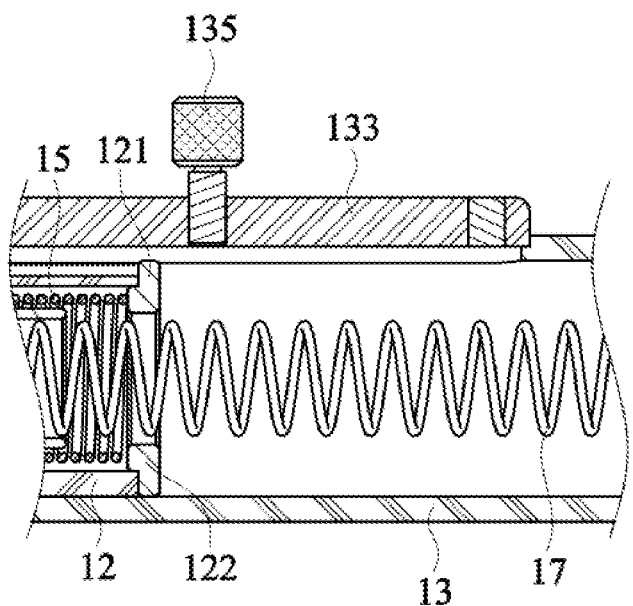
FIG. 9B is the second schematic diagram of the second gear change of the preferred embodiment of the present invention.

Please refer to FIG. 8A, FIG. 8B, FIG. 9A and FIG. 9B at the same time, wherein FIG. 8A is one of the schematic diagrams of the first gear change of the preferred embodiment of the present invention, FIG. 8B is the second schematic diagram of the first gear change in the preferred embodiment of the present invention, FIG. 9A is one of the schematic diagrams of the second gear change of the preferred embodiment of the present invention, and FIG. 9B is the second schematic diagram of the second gear change in the preferred embodiment of the present invention. Please also refer to FIGS. 1 to 5 at the same time.

In this embodiment, the sliding key 133 of the second rod member 13 includes a gear control member 135, and the gear control member 135 is selectively placed at different positions of the sliding key 133 and is selectively blocked by the blocking piece 122. The aforementioned gear control member 135 is a screw in this embodiment.

In detail, the gear control member 135 can be set in different positions of the sliding key 133, such as the first gear position shown in FIGS. 8A and 8B and the second gear position shown in FIGS. 9A and 9B, when the second rod member 13 slides relative to the first rod member 12, that is, when the sliding key 133 slides in the sliding groove 123 correspondingly, the gear control member 135 on the sliding key 133 can be used to block the blocking piece 122 of the first rod member 12. Because the gear control member 135 is selectively arranged on different positions of the sliding key 133 to produce different distance changes, the sliding distance of the second rod member 13 relative to the first rod member 12 therefore produces different changes (as shown in FIG. 8A and FIG. 9A).

According to actual needs, the gear control member 135 unnecessarily is blocked by the blocking piece 122 of the first rod member 12, and the gear control member 135 can be set to a height (For example, in this embodiment, the gear control member 135 (screw) is screwed up). When the second rod member 13 slides relative to the first rod member 12, the gear control member 135 can go over the blocking piece 122 of the first rod member 12 without being blocked by the blocking piece 122 (as shown in FIG. 8B and FIG. 9B).

Figure 10:
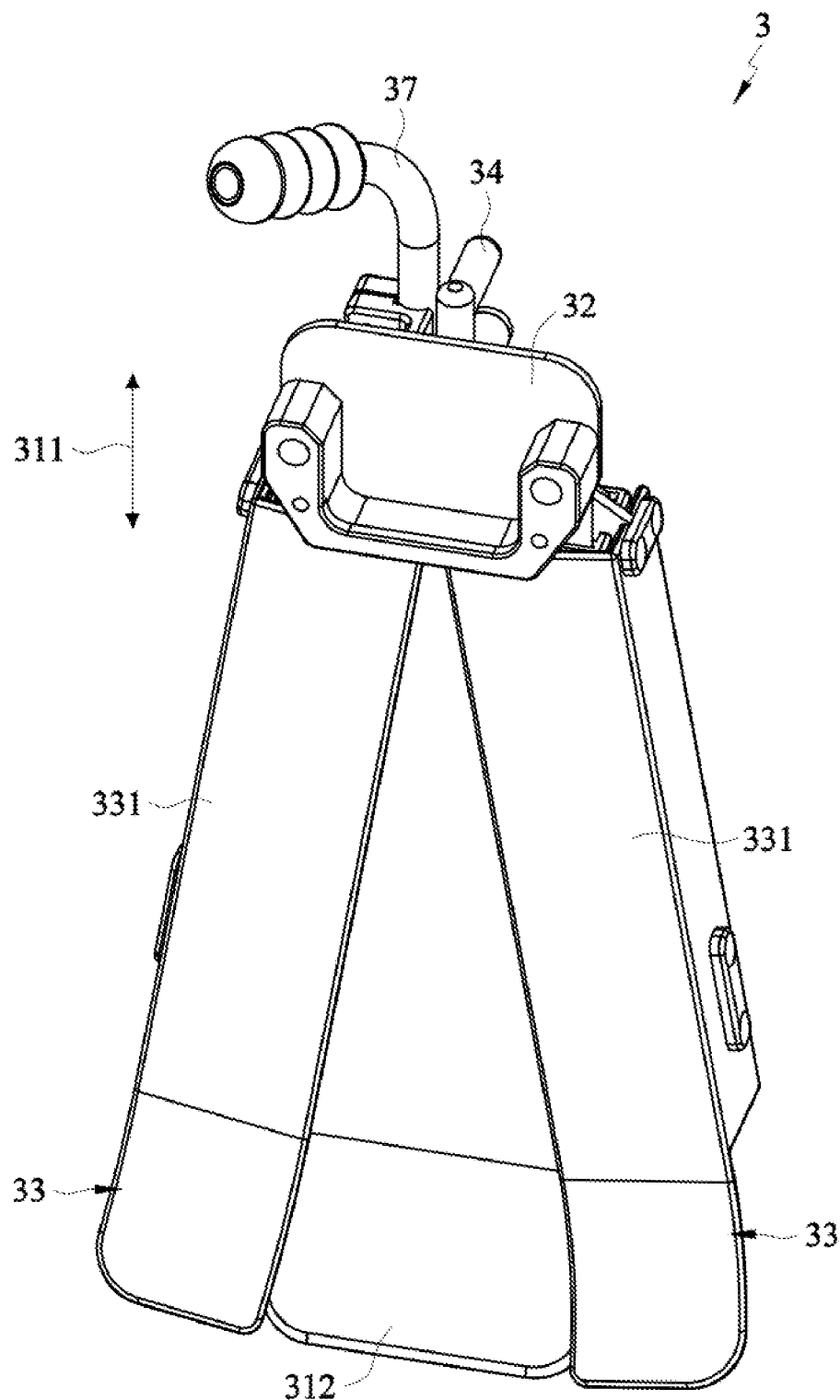
FIG. 10 is a perspective view of another preferred embodiment of the present invention.
Figure 11:
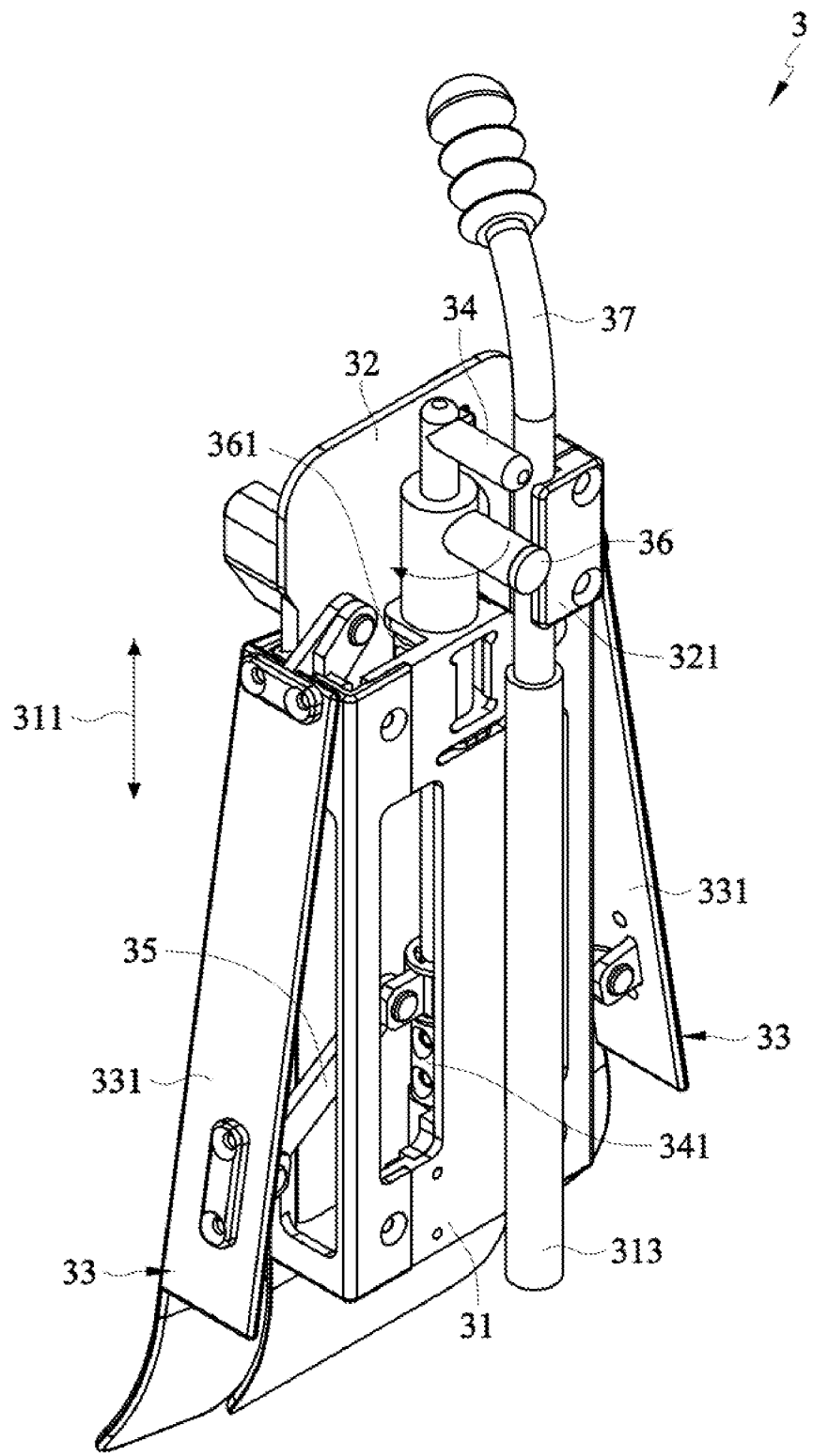
FIG. 11 is a perspective view of another preferred embodiment of the present invention from another perspective.

Please refer to FIGS. 10 and 11 at the same time, wherein FIG. 10 is a perspective view of another preferred embodiment of the present invention, and FIG. 11 is a perspective view of another preferred embodiment of the present invention from another perspective.

As shown in FIG. 10 and FIG. 11, the surgical retractor 3 of another embodiment includes a mounting base 31, a sliding sheet 32, an expansion member 33, a shaft member 34, and two connecting rod members 35 and a bush 36. Wherein, the mounting base 31 defines a longitudinal direction 311 and includes a blade body 312; the sliding sheet 32 is attached to the mounting base 31 and slides along the longitudinal direction 311 relative to the mounting base 31; the expansion member 33 includes two expansion blades 331, which are respectively arranged on opposite sides of the mounting base 31 and pivoted relative to the mounting base 31; the shaft member 34 is arranged on the mounting base 31 and is relative to the mounting base 31, the shaft member 34 slides in the longitudinal direction 311 and rotates around the longitudinal direction 311, and the shaft member 34 includes a shaft cam 341, the shaft cam 341 selectively abuts against the blade body 312; two connecting rod members 35 (in FIG. 11, because of the viewing angle relationship only shows one of the connecting rod members 35) are respectively connected between the shaft member 34 and the two expansion blades 331; the bush 36 is arranged on the mounting base 31 and rotates around the longitudinal direction 311, and the bush 36 includes a bushing cam 361, which selectively abuts against the blade body 312. The aforementioned shaft member 34 and the bush 36 are coaxially arranged in this embodiment.

As shown in FIG. 11, in this embodiment, the mounting base 31 is provided with a hollow rod member 313 along the longitudinal direction 311, and the surgical retractor 3 further includes a suction tube 37. A part of the suction tube 37 is arranged in the hollow rod member 313 and slides relative to the hollow rod member 313. In addition, the aforementioned sliding sheet 32 is provided with a suction tube clamp 321, and the suction tube clamp 321 clamps the suction tube 37.

The above-mentioned surgical retractor 3 can have different usage states in actual use, as detailed below.

Figure 12:
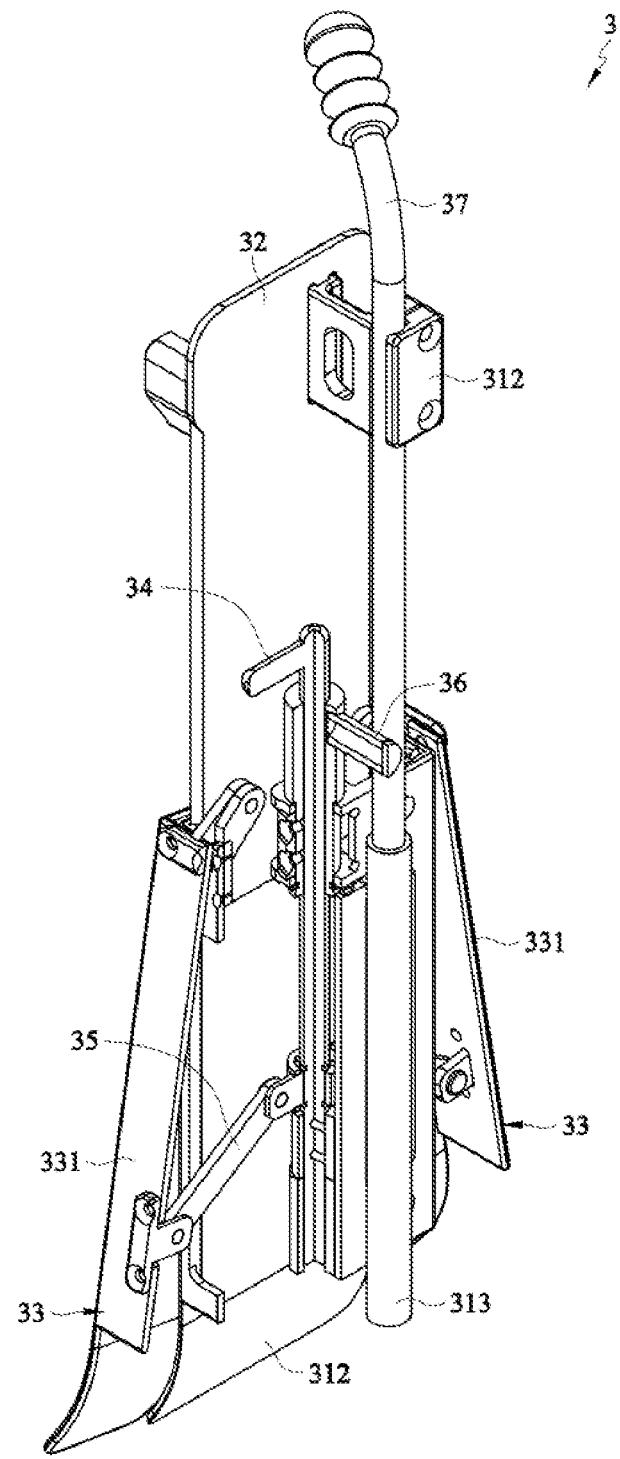
FIG. 12 is one of the schematic diagrams of the use state of another preferred embodiment of the present invention.

Please refer to FIG. 12, which is one of the schematic diagrams of the use state of another preferred embodiment of the present invention. Please also refer to FIG. 10 and FIG. 11 at the same time. The rear part of the mounting base 31 is not shown for easy description.

As shown in FIG. 12, in one of the use states, the user (not shown) can hold the sliding sheet 32 with one hand and the bush 36 with the other hand, so that the mounting base 31 and the blade body 312 installed therein and the two expansion blades 331 move downwards, while the sliding sheet 32 moves relatively upwards, and while moving downwards, the suction tube 37 is clamped by the suction tube clamp 321, and the hollow rod member 313 is also following the downward movement of the mounting base 31 (including the blade body 312), that is, a part of the suction tube 37 slides upward relative to the hollow rod member 313, so that the purpose of the suction tube 37 can be expanded and contracted freely. When moving to the required position, the bush 36 is rotated in the direction of the arrow shown in FIG. 12, the bush 36 rotates around the longitudinal direction 311, until the bush cam 361 abuts the blade body 312 to achieve clamping. The purpose is to make the blade body 312 immobile; on the contrary, rotating the bush 36 around the longitudinal direction 311 in the opposite direction can make the bush cam 361 separate from the blade body 312 and make the blade body 312 movable.

Figure 13:
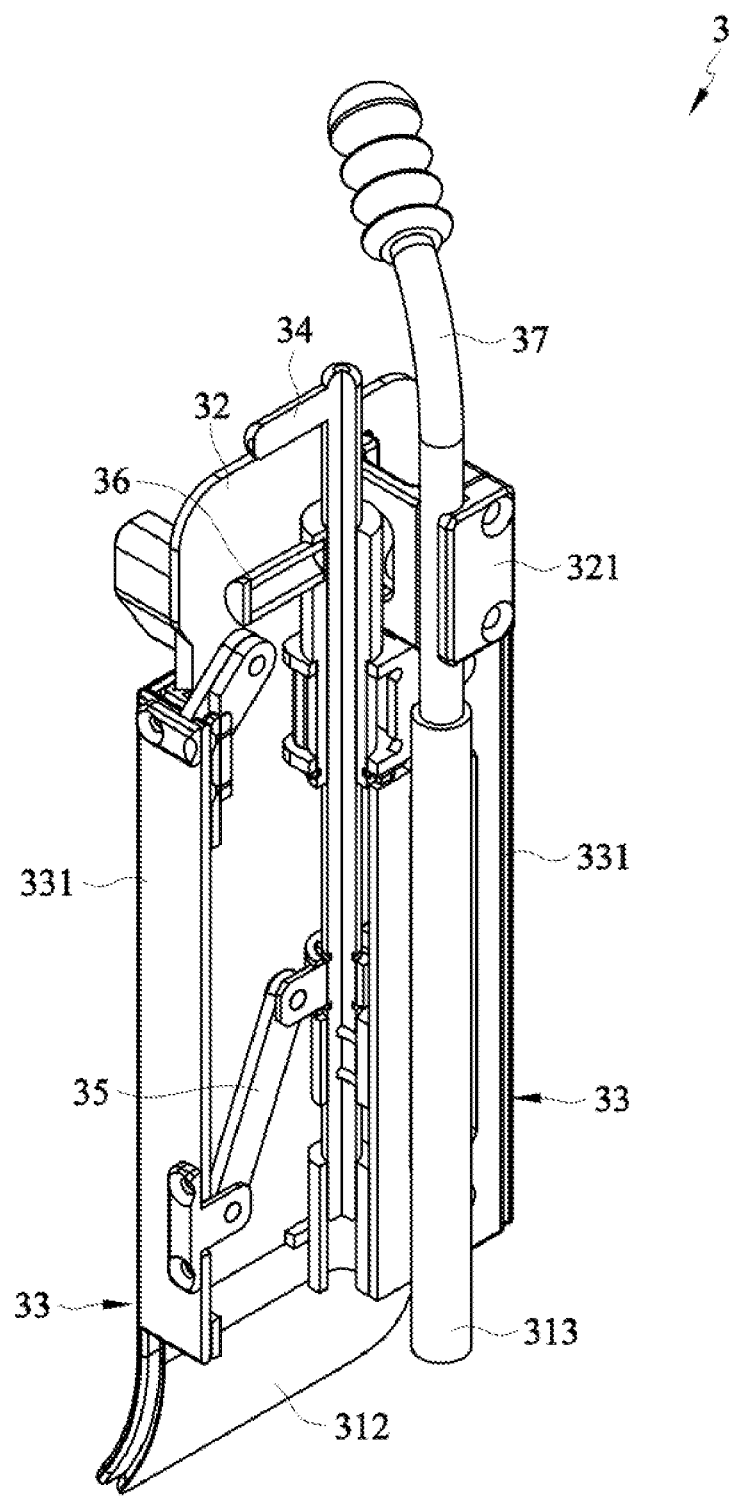
FIG. 13 is the second schematic diagram of the use state of another preferred embodiment of the present invention, wherein two expansion blades are shown in a folded state.
Figure 14:
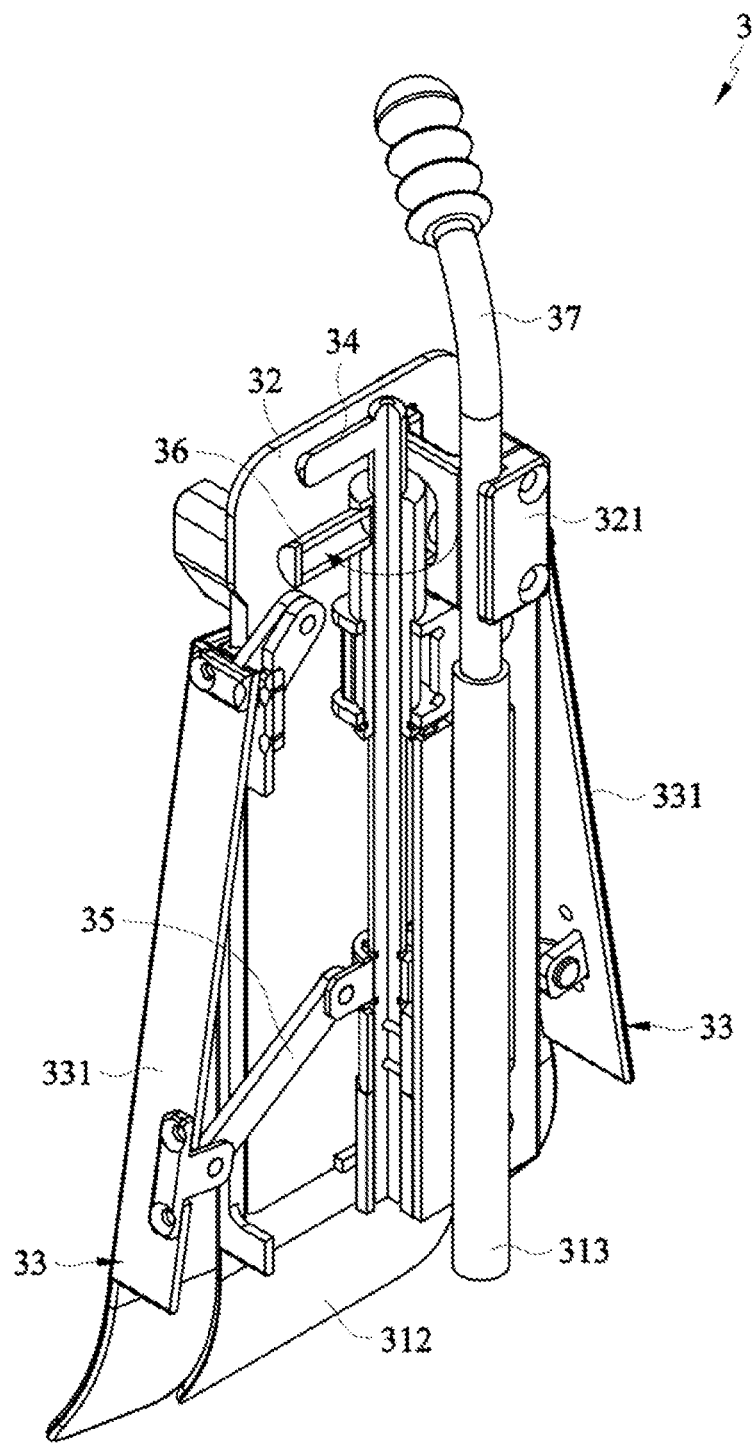
FIG. 14 is the third schematic diagram of the use state of another preferred embodiment of the present invention, wherein two expansion blades are shown in the unfolded state.

Please refer to FIG. 13 and FIG. 14 at the same time. FIG. 13 is the second schematic diagram of the use state of another preferred embodiment of the present invention, which shows that the two expansion blades are in a folded state. FIG. 14 is the third schematic diagram of the use state of another preferred embodiment of the present invention, which shows that the two expansion blades are in the unfolded state, and please refer to FIG. 10 and FIG. 11 at the same time. Similarly, the rear part of the mounting base 31 is not shown in FIGS. 13 and 14 for easy description.

In another use state, the shaft member 34 can be slid along the longitudinal direction 311 relative to the mounting base 31 to drive the two connecting rod members 35 to respectively drive the two expansion blades 331 to pivot relative to the mounting base 31. In detail, when the shaft member 34 is moved downward, the sliding of the shaft member 34 will drive the two connecting rod members 35 to move, because the two expansion blades 331 are respectively (for example, by a pivot shaft) provided on the two opposite sides of the mounting base 31 and respectively pivot relative to the mounting base 31, so the two connecting rod members 35 will drive the two expansion blades 331 to expand, as shown in FIG. 14; on the contrary, when the shaft member 34 is moved upward, the two expansion blades 331 will be folded due to the driving of the two connecting rod members 35, as shown in FIG. 13. Similarly, when the shaft member 34 is moved and the two expansion blades 331 are expanded or folded to the required position, the shaft member 34 is rotated in the direction of the arrow shown in FIGS. 13 and 14 until the shaft cam 341 abuts against the blade body 312 to achieve the purpose of clamping, so that the two expansion blades 331 are fixed in the desired position; on the contrary, like the bush 36 described above, rotating the shaft member 34 in the opposite direction can disengage the shaft cam 341 without abutting against the blade body 312.

From FIG. 12, FIG. 13 and FIG. 14, it can be seen that the expansion and folding of the two expansion blades 331 is not related to the movement of the blade body 312, and the two actions can be operated independently, that is, the expansion and folding of two expansion blades 331 is related to the movement of the shaft member 34 (and its shaft cam 341). The relative up and down movement and fixing of the blade body 312 and the sliding sheet 32 are related to the bush 36 (and its bush cam 361).

In addition, in actual use, the above-mentioned surgical retractor 3 can be made of stainless steel, which can easily complete the disinfection operation after medical use. In addition, the above-mentioned surgical retractor 3 has a lot of large-area space in actual design, so blood stains contaminated during the operation can be brushed off, that is, the above-mentioned surgical retractor 3 can facilitate the brush to brush up and down, so as to reduce the disinfection time.

The above descriptions are only preferred embodiments of the present invention, and are not intended to limit the present invention. Any modification, equivalent replacement, improvement, etc. made within the spirit and principle of the present invention shall include within the protection scope of the present invention.

What is claimed is:
1. A surgical retractor, comprising:
a mounting base;
a first rod member, one end of the first rod member assembled on the mounting base, and the other end of the first rod member comprising a blocking part;
a connecting member, the connecting member assembled on the first rod member, and the connecting member comprising a shoulder and a first connecting part;
a compression spring, the compression spring arranged on the connecting member and abutting against the shoulder and the blocking part;
a second rod member, the second rod member slidably disposed on the first rod member and sliding relative to the first rod member, and one end of the second rod member sliding and extending out relative to the first rod member;

an expansion member, the expansion member assembled at the one end of the second rod member, and the expansion member comprising a second connecting part;

an extension spring connecting the first connecting part and the second connecting part; and a position member assembled on the second rod member and selectively abutting against the first rod member.

2. The surgical retractor according to claim 1, wherein the mounting base comprises a fixing base and a clamping arm, and the clamping arm extends outward from the fixing base.

3. The surgical retractor according to claim 1, wherein the blocking part is formed on a blocking piece, and the first rod member comprises a sliding groove, the second rod member comprises a sliding key, and the second rod member is slidably disposed on the first rod member by the sliding groove corresponding to the sliding key sliding thereon.

4. The surgical retractor according to claim 3, wherein the sliding key comprises a blocking protrusion, and the blocking protrusion is blocked by the blocking piece; the sliding key comprises a gear control member, and the gear control member is selectively arranged at different positions of the sliding key and selectively blocked by the blocking piece.

5. The surgical retractor according to claim 1, wherein the connecting member comprises a series part and a parallel part, the series part is formed with the shoulder and the first connecting part; the compression spring comprises a left compression spring and a right compression spring, and the left compression spring and the right compression spring are arranged in the parallel part in parallel.

6. The surgical retractor according to claim 1, wherein the expansion member comprises an expansion blade, a suction tube, and a fixing member arranged with each other, and the fixing member is formed with the second connecting part; the position member is a knob, and the knob is screwed on the second rod member and selectively screwed against the first rod member; the first rod member and the second rod member are each a tubular member, and the second rod member is sleeved outside the first rod member.

\* \* \* \* \*